US006051550A

United States Patent [19]
Schnepf et al.

[11] Patent Number: 6,051,550
[45] Date of Patent: Apr. 18, 2000

[54] MATERIALS AND METHODS FOR CONTROLLING HOMOPTERAN PESTS

[75] Inventors: H. Ernest Schnepf; Brian Stockhoff, both of San Diego, Calif.

[73] Assignee: Mycogen Corporation, San Diego, Calif.

[21] Appl. No.: 09/128,318

[22] Filed: Aug. 3, 1998

Related U.S. Application Data

[60] Provisional application No. 60/055,440, Aug. 8, 1997.

[51] Int. Cl.[7] .......................... A01N 61/00; A01N 63/00; A61K 38/00; C12N 5/04; C12N 5/10
[52] U.S. Cl. .......................... 514/2; 514/12; 424/93.461; 435/419
[58] Field of Search .................................. 435/253, 419; 424/93.461; 536/23.71; 514/12, 2

[56] References Cited

U.S. PATENT DOCUMENTS

| | | | |
|---|---|---|---|
| 4,448,885 | 5/1984 | Schnepf et al. | 435/253 |
| 4,467,036 | 8/1984 | Schnepf et al. | 435/317 |
| 4,990,332 | 2/1991 | Payne et al. | 424/93 |
| 5,039,523 | 8/1991 | Payne et al. | 424/93 |
| 5,126,133 | 6/1992 | Payne et al. | 424/93 |
| 5,164,180 | 11/1992 | Payne et al. | 424/93 |
| 5,169,629 | 12/1992 | Payne et al. | 424/93 |
| 5,185,148 | 2/1993 | Michaels | 424/93 |
| 5,262,158 | 11/1993 | Payne et al. | 424/93 |
| 5,262,159 | 11/1993 | Payne et al. | 424/93 |
| 5,273,746 | 12/1993 | Payne et al. | 424/93 |
| 5,277,905 | 1/1994 | Foncerrada et al. | 424/93 |
| 5,286,485 | 2/1994 | Uyeda et al. | 424/93 |
| 5,366,892 | 11/1994 | Foncerrada et al. | 435/252.33 |
| 5,424,410 | 6/1995 | Payne et al. | 536/23.71 |
| 5,457,179 | 10/1995 | Foncerrada et al. | 530/350 |
| 5,468,636 | 11/1995 | Payne et al. | 435/252.3 |
| 5,554,534 | 9/1996 | Michaels et al. | 435/252.3 |

FOREIGN PATENT DOCUMENTS

| | | | |
|---|---|---|---|
| 9405771 | 3/1994 | WIPO . | |
| 9424264 | 10/1994 | WIPO . | |
| WO 95/16778 | 6/1995 | WIPO | C12N 15/32 |

OTHER PUBLICATIONS

Cousin, Marie–Therese (1995) "Phytoplasma and phytoplasmonis . II. Diagnosis and control method," 6001 *Chemical Abstracts*, vol. 123, No. 7, p. 361.

Gleave, A.P., et al. (1992) "Identification of an Insecticidal Crystal Protein from *Bacillus thuringiensis* DS1R517 with Significant Sequence Differences from Previously Described Toxins" Journal of General Microbiology 138:55–62.

Shevelev, A.B., et al. (1993) "Primary Structure of cryX**, the Novel δ–Endotoxin–Related Gene from *Baccillus thuringiensis* spp. *galleriae*" FEBS Lett. 336(1):79–82.

Smulevitch, S.V., et al. (1991) "Nucleotide Sequence of a Novel δ–Endotoxin Gene crylg of *Bacillus thuringiensis* spp. *galleriae*" FEBS Lett 293(1.2):25–28.

Lambert, B., et al. (1996) "A *Bacillus thuringiensis* Insecticidal Crystal Protein with a High Activity Against Members of the Family Noctuidae" Applied Environmental Microbiology 62(1):80–86.

Gaertner, F.H. (1989) "Cellular Delivery Systems for Insecticidal Proteins: Living and Non–Living Microorganisms," in *Controlled Delivery of Crop Protection Agents*, R.M. Wilkins, ed., Taylor and Francis, New York and London, 1990, pp. 245–255.

Couch, T.L., (1980) "Mosquito Pathogenicity of *Bacillus thuringiensis* var. *israelensis*" Developments in Industrial Microbiology 22:61–76.

Beegle, C.C. (1978) "Use of Entomogenous Bacteria in Agroecosystems," *Developments in Industrial Microbiology* 20:97–104.

Krieg, A., et al. (1983) "*Bacillus thuringiensis* var. *tenebrionsis*, a New Pathotype Effective Against Larvae of Coleoptera" Z. Ang. Ent. 96:500–508.

Schnepf, H.E., H.R. Whiteley (1981) "Cloning and Expression of the *Bacillus thuringiensis* Crystal Protein Gene in *Escherichia Coli*" Proc. Natl. Acad. Sci. USA 78(5):2893–2897.

Gaertner, F.H., L.Kim (1988) "Current Applied Recombinant DNA Projects" TIBTECH 6(4):54–57.

Hofte, H., H.R. Whiteley (1989) "Insecticidal Crystal Proteins of *Bacillus thuringiensis*" Microbiological Review 53(2):242–255.

Feitelson, J.S., et al. (1992) "*Bacillus thuringiensis*: Insects and Beyond" Biotechnology 10:271–275.

Beegle, C.C., T. Yamamoto (1992) "History of *Bacillus thuringiensis* Berliner Research and Development" Can. Ent. 124:587–616.

*Primary Examiner*—Karen Cochrane Carlson
*Assistant Examiner*—Devesh Srivastava
*Attorney, Agent, or Firm*—Saliwanchik, Lloyd & Saliwanchik

[57] ABSTRACT

The subject invention concerns materials and methods for the control of non-mammalian pests. In specific embodiments, the subject invention concerns materials and methods useful in the control of insects from the Order Homoptera. More specifically, the subject invention provides novel *Bacillus thuringinesis* (B.t.) isolates, or strains, toxins, and toxin-encoding genes that are useful for the control of homopterans. The strains HD969, PS66D3, and PS50C are specifically exemplified herein as yielding mortality against homopterans. In a preferred embodiment, the target pests are selected from the group consisting of leafhoppers and planthoppers.

3 Claims, No Drawings

MATERIALS AND METHODS FOR CONTROLLING HOMOPTERAN PESTS

CROSS-REFERENCE TO A RELATED APPLICATION

This application claims priority from U.S. provisional patent application Ser. No. 60/055,440, filed Aug. 8, 1997.

BACKGROUND OF THE INVENTION

The soil microbe *Bacillus thuringiensis* (B.t.) is a Gram-positive, spore-forming bacterium traditionally characterized by parasporal crystalline protein inclusions. These inclusions often appear microscopically as distinctively shaped crystals. The proteins can be highly toxic to pests and specific in their toxic activity. Certain B.t. toxin genes have been isolated and sequenced, and recombinant DNA-based B.t. products have been produced and approved for use. In addition, with the use of genetic engineering techniques, new approaches for delivering B.t. toxins to agricultural environments are under development, including the use of plants genetically engineered with endotoxin genes for insect resistance and the use of stabilized intact microbial cells as B.t. toxin delivery vehicles (Gaertner, F. H., L. Kim [1988] *TIBTECH* 6:S4–S7; Beegle, C. C., T. Yamamoto, "History of *Bacillus thuringiensis* Berliner research and development," *Can. Ent.* 124:587–616). Thus, isolated B.t. toxin genes have increasing commercial value.

Until fairly recently, commercial use of B.t. pesticides has been largely restricted to a narrow range of lepidopteran (caterpillar) pests. Preparations of the spores and crystals of *B. thuringiensis* subsp. *kurstaki* have been used for many years as commercial insecticides for lepidopteran pests. For example, *B. thuringiensis* var. *kurstaki* HD-1 produces a crystalline δ-endotoxin which is toxic to the larvae of a number of lepidopteran insects.

Investigators have now discovered B.t. pesticides with specificities for a broader range of pests. For example, other species of B.t., namely *israelensis* and *morrisoni* (a.k.a. tenebrionis, a.k.a. B.t. M-7, a.k.a. B.t. san diego), have been used commercially to control insects of the orders Diptera and Coleoptera, respectively (Gaertner, F. H. [1989] "Cellular Delivery Systems for Insecticidal Proteins: Living and Non-Living Microorganisms," in *Controlled Delivery of Crop Protection Agents*, R. M. Wilkins, ed., Taylor and Francis, New York and London, 1990, pp. 245–255.). See also Couch, T. L. (1980) "Mosquito Pathogenicity of Bacillus thuringiensis var. israelensis," *Developments in Industrial Microbiology* 22:61–76; and Beegle, C. C. (1978) "Use of Entomogenous Bacteria in Agroecosystems," *Developments in Industrial Microbiology* 20:97–104. Krieg, A., A. M. Huger, G. A. Langenbruch, W. Schnetter (1983) *Z. ang. Ent.* 96:500–508 describe *Bacillus thuringiensis* var. *tenebrionis*, which is reportedly active against two beetles in the order Coleoptera. These are the Colorado potato beetle, *Leptinotarsadecemlineata*, and *Agelastica alni*.

More recently, new subspecies of B.t. have been identified, and genes responsible for active δ-endotoxin proteins have been isolated (Höfte, H., H. R. Whiteley [1989] *Microbiological Reviews* 52(2):242–255). Höfte and Whiteley classified B.t. crystal protein genes into four major classes. The classes were cryI (Lepidoptera-specific), cryII (Lepidoptera- and Diptera-specific), cryIII (Coleoptera-specific), and cryIV (Diptera-specific).

The discovery of strains specifically toxic to other pests has been reported (Feitelson, J. S., J. Payne L. Kim [1992] *Bio/Technology* 10:271–275). cryV has been proposed to designate a class of toxin genes that are nematode-specific. Lambert et al. (Lambert, B., L. Buysse, C. Decock, S. Jansens, C. Piens, B. Saey, J. Seurinck, K. van Audenhove, J. Van Rie, A. Van Vliet, M. Peferoen [1996] *Appl. Environ. Microbiol* 62(1):80–86) describe the characterization of a Cry9 toxin active against lepidopterans. Published PCT applications WO 94/05771 and WO 94/24264 also describe B.t. isolates active against lepidopteran pests. U.S. Pat. No. 5,273,746 discloses several B.t. isolates, including PS192M4, as having activity against lice. Gleave et al. ([1991] *JGM* 138:55–62), Shevelev et al. ([1993] *FEBS Lett.* 336:79–82; and Smulevitch et al. ([1991] *FEBS Lett.* 293:25–26) also describe B.t. toxins. Many other classes of B.t. genes have now been identified.

The cloning and expression of a B.t. crystal protein gene in *Escherichia coli* has been described in the published literature (Schnepf, H. E., H. R. Whiteley [1981] *Proc. Natl. Acad. Sci. USA* 78:2893–2897.). U.S. Pat. No. 4,448,885 and U.S. Pat. No. 4,467,036 both disclose the expression of B.t. crystal protein in *E. coli*. U.S. Pat. Nos. 4,990,332; 5,039,523; 5,126,133; 5,164,180; and 5,169,629 are among those which disclose B.t. toxins having activity against lepidopterans.

U.S. Pat. Nos. 5,262,159 and 5,468,636 disclose B.t. isolates PS157C1, PS86A1, and PS75J1 for use against aphids. U.S. Pat. Nos. 5,277,905 and 5,457,179 disclose the use of B.t. isolate PS50C for use against coleopteran pests. U.S. Pat. No. 5,366,892 discloses the sequence of the 50C(a) B.t. toxin. U.S. Pat. No. 5,286,485 discloses the use of PS50C against lepidopteran pests. U.S. Pat. No. 5,185,148 discloses the use of PS50C against scarab pests. U.S. Pat. No. 5,554,534 discloses the sequence of the 50C(b) B.t. toxin. U.S. Pat. Nos. 5,262,158 and 5,424,410 disclose the use of PS50C against acarides.

As a result of extensive research and investment of resources, other patents have issued for new B.t. isolates and new uses of B.t. isolates. See Feitelson et al., supra, for a review. However, the discovery of new B.t. isolates and new uses of known B.t. isolates remains an empirical, unpredictable art.

Insects belonging to the order Homoptera include piercing and sucking insects such as leafhoppers and planthoppers. Leafhoppers and planthoppers share a close evolutionary relationship. Leafhoppers and planthoppers are found worldwide and cause serious economic loss to crops and ornamental plants via feeding damage and disease vectoring. A specific example of a planthopper is the brown rice planthopper (*Nilaparvata lugens*). Because of their piercing and sucking feeding habits, planthoppers and leafhoppers are not readily susceptible to foliar applications of *Bacillus thuringiensis* (B.t.) proteins in their native, crystal states.

BRIEF SUMMARY OF THE INVENTION

The subject invention concerns materials and methods for the control of non-mammalian pests. In specific embodiments, the subject invention concerns materials and methods useful in the control of insects from the Order Homoptera. More specifically, the subject invention provides novel *Bacillus thuringinesis* (B.t.) isolates, or strains, toxins, and toxin-encoding genes that are useful for the control of homopterans. The B.t. strains HD969, PS66D3, and PS50C are specifically exemplified herein as being toxic to homopterans. In a preferred embodiment, the target pests are selected from the group consisting of leafhoppers and planthoppers.

Nucleotide sequences useful according to the subject invention encode pesticidal toxins. One embodiment of the subject invention concerns plants cells transformed with at least one polynucleotide sequence of the subject invention such that the transformed plant cells express pesticidal toxins in tissues consumed by the target pests. Such transformation of plants can be accomplished using techniques well known to those skilled in the art and would typically involve modification of the gene to optimize expression of the toxin in plants.

Alternatively, the B.t. isolates of the subject invention, or recombinant microbes expressing the toxins described herein, can be used to control pests. In this regard, the invention includes the treatment of substantially intact B.t. cells, and/or recombinant cells containing the expressed toxins of the invention, treated to prolong the pesticidal activity when the substantially intact cells are applied to the environment of a target pest. The treated cell acts as a protective coating for the pesticidal toxin. The toxin becomes active upon ingestion by a target insect.

Crystallized B.t. protein toxins can be used in agricultural applications for the control of pests, with application methods and formulations that are well known in the art. In one embodiment, the subject invention further provides protein toxins that are solubilized. The toxins of the subject invention are distinguishable from B.t. exotoxins, which have non-specific, broad-spectrum activity.

As described herein, the toxins useful according to the subject invention may be chimeric toxins produced by combining portions of multiple toxins. Also, toxins of the subject invention may be used in combination to achieve enhanced pest control.

DETAILED DISCLOSURE OF THE INVENTION

The subject invention provides B.t. isolates and toxins active against homopterans including leafhoppers and planthoppers. Specific isolates useful according to the subject invention are designated PS50C, PS66D3, and HD969. Some of the characteristics of these strains are presented in Table 1.

TABLE 1

| Strain | Inclusion Type | H-Serotype | SDS-PAGE Protein Profile |
|---|---|---|---|
| PS50C | Sphere | 18, kumamotoensis | 133,128 |
| PS66D3 | Flattish, Almost Square | 8 | 75,66,(58) |
| HD969 | BP to lemon to amorphic | 6 | 130(s) |

PS66D3 is a novel isolate. This microorganism has been deposited in the permanent collection of the Agricultural Research Service Patent Culture Collection (NRRL), Northern Regional Research Center 1815 North University Street, Peoria, Ill. 61604, USA. The culture repository numbers of the deposited strains are:

| Culture | Repository Number | Deposit Date |
|---|---|---|
| Bacillus thuringiensis PS66D3 | NRRL B-21657 | February 19, 1997 |

The isolates for use according to the subject invention has been deposited under conditions that assure that access to the cultures will be available during the pendency of this patent application to one determined by the Commissioner of Patents and Trademarks to be entitled thereto under 37 CFR 1.14 and 35 U.S.C. 122. The deposits are available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposits will be stored and made available to the public in accord with the provisions of the Budapest Treaty for the Deposit of Microorganisms, i. e., they will be stored with all the care necessary to keep them viable and uncontaminated for a period of at least five years after the most recent request for the furnishing of a sample of a deposit, and in any case, for a period of at least 30 (thirty) years after the date of deposit or for the enforceable life of any patent which may issue disclosing the cultures. The depositor acknowledges the duty to replace the deposit (s) should the depository be unable to furnish a sample when requested, due to the condition of the deposit(s). All restrictions on the availability to the public of the subject culture deposits will be irrevocably removed upon the granting of a patent disclosing them.

The following isolate, and clones containing genes therefrom, are available to the public by virtue of the issuance of U.S. patents. These isolates and the corresponding U.S. Patents are:

| Culture | Accession Number | Deposit Date | Pat. Nos. |
|---|---|---|---|
| B. thuringiensis PS50C | NRRL B-18746 | January 9, 1991 | 5,457,179 5,277,905 5,286,485 5,185,148 |
| E. coli NM522 (pMYC1638) (MR605) [50C(a)] | NRRL B-18751 | January 11, 1991 | 5,366,892 5,262,158 5,424,410 |
| E. coli NM522 (pMYC1650) [50C(b)] | NRRL B-21023 | December 4, 1992 | 5,554,534 |

These patents, with their disclosure of the indicated isolates as well as their toxins and genes, are incorporated herein by reference.

The isolate H1D969 is available from the USDA-ARS NRRL Culture Collection, Peoria, Ill. (United States Department of Agriculture, Agricultural Research Service Culture Collection, Microbial Properties Research Unit, National Center for Agricultural Utilization Research, 1815 N. University Street, Peoria, Ill. 61604; Accession No. NRRL HD-969). HD969 has numerous Cry1 genes, including 1Ac, 1B, and 1C. PCR signatures for cry 7,8,9 class gene(s) have also been found. PS66D3 makes a 72 and 64 kDa set of proteins (a typical 3A, 3B pattern).

The strains HD969, PS66D3, and PS50C yielded mortality of N. lugens nymphs that were substantially greater after 72 hours than that obtained with negative controls.

Genes and toxins. A further aspect of the subject invention concerns novel toxins and genes obtainable from the isolates for use according to the subject invention.

The toxins and polynucleotide sequences of the subject invention are defined according to several parameters. One critical characteristic of the toxins described herein is pesticidal activity. In a specific embodiment, these toxins have activity against homopteran pests. The toxins and genes of the subject invention can be further defined by their amino acid and nucleotide sequences. The sequences of the molecules can be defined in terms of homology or identity to certain exemplified sequences as well as in terms of the ability to hybridize with, or be amplified by, certain exemplified probes and primers. The toxins provided herein can also be identified based on their immunoreactivity with certain antibodies. With the teachings provided herein, one skilled in the art could readily produce and use the various toxins and polynucleotide sequences described herein.

The genes and toxins useful according to the subject invention include not only the full length sequences but also fragments of these sequences, variants, mutants, and fusion proteins which retain the characteristic pesticidal activity of the novel toxins specifically exemplified herein. As used herein, the terms "variants" or "variations" of genes refer to nucleotide sequences which encode the same toxins or which encode equivalent toxins having pesticidal activity. As used herein, the term "equivalent toxins" refers to toxins having the same or essentially the same biological activity against the target pests as the exemplified toxins.

It should be apparent to a person skilled in this art that genes encoding active toxins can be identified and obtained through several means. The specific genes exemplified herein may be obtained from the isolates deposited at a culture depository as described above. These genes, or portions or variants thereof, may also be constructed synthetically, for example, by use of a gene synthesizer. Variations of genes may be readily constructed using standard techniques for making point mutations. Also, fragments of these genes can be made using commercially available exonucleases or endonucleases according to standard procedures. For example, enzymes such as Bal31 or site-directed mutagenesis can be used to systematically cut off nucleotides from the ends of these genes. Also, genes which encode active fragments may be obtained using a variety of restriction enzymes. Proteases may be used to directly obtain active fragments of these toxins.

Equivalent toxins and/or genes encoding these equivalent toxins can be derived from B.t. isolates and/or DNA libraries using the teachings provided herein. There are a number of methods for obtaining the pesticidal toxins of the instant invention. For example, antibodies to the pesticidal toxins disclosed and claimed herein can be used to identify and isolate other toxins from a mixture of proteins. Specifically, antibodies may be raised to the portions of the toxins which are most constant and most distinct from other B.t. toxins. These antibodies can then be used to specifically identify equivalent toxins with the characteristic activity by immunoprecipitation, enzyme linked immunosorbent assay (ELISA), or western blotting. Antibodies to the toxins disclosed herein, or to equivalent toxins, or fragments of these toxins, can readily be prepared using standard procedures in this art. The genes which encode these toxins can then be obtained from the microorganism.

Fragments and equivalents which retain the pesticidal activity of the exemplified toxins would be within the scope of the subject invention. Also, because of the redundancy of the genetic code, a variety of different DNA sequences can encode the amino acid sequences disclosed herein. It is well within the skill of a person trained in the art to create these alternative DNA sequences encoding the same, or essentially the same, toxins. These variant DNA sequences are within the scope of the subject invention. As used herein, reference to "essentially the same" sequence refers to sequences which have amino acid substitutions, deletions, additions, or insertions which do not materially affect pesticidal activity. Fragments retaining pesticidal activity are also included in this definition.

Certain toxins of the subject invention have been specifically exemplified herein. Since these toxins are merely exemplary of the toxins of the subject invention, it should be readily apparent that the subject invention also relates to variants or equivalents of novel genes and toxins having the same or similar pesticidal activity of the exemplified novel toxins. Equivalent toxins will have amino acid homology with a novel exemplified toxin. These equivalent genes and toxins will typically have greater than 60% identity with the sequences specifically exemplified herein; preferably, there will be more than 75% identity, more preferably greater than 80%, most preferably greater than 90%, and the identity can be greater than 95%. The amino acid homology will be highest in critical regions of the toxin which account for biological activity or are involved in the determination of three-dimensional configuration which ultimately is responsible for the biological activity. In this regard, certain amino acid substitutions are acceptable and can be expected if these substitutions are in regions which are not critical to activity or are conservative amino acid substitutions which do not affect the three-dimensional configuration of the molecule. For example, amino acids may be placed in the following classes: non-polar, uncharged polar, basic, and acidic. Conservative substitutions whereby an amino acid of one class is replaced with another amino acid of the same type fall within the scope of the subject invention so long as the substitution does not materially alter the biological activity of the compound. Table 2 provides a listing of examples of amino acids belonging to each class.

TABLE 2

| Class of Amino Acid | Examples of Amino Acids |
| --- | --- |
| Nonpolar | Ala, Val, Leu, Ile, Pro, Met, Phe, Trp |
| Uncharged Polar | Gly, Ser, Thr, Cys, Tyr, Asn, Gln |
| Acidic | Asp, Glu |
| Basic | Lys, Arg, His |

In some instances, non-conservative substitutions can also be made. The critical factor is that these substitutions must not significantly detract from the biological activity of the toxin.

The toxins of the subject invention can also be characterized in terms of the shape and location of toxin inclusions, which are described above. Although crystal proteins are commonly used in the art, isolates for use according to the subject invention can also be grown under conditions that facilitate the secretion of toxins. Thus, the supernatant from these cultures can be used to obtain toxins according to the subject invention. Thus, the subject invention is not limited to crystal proteins; useful soluble proteins are also contemplated.

As used herein, reference to "isolated" polynucleotidesand/or "purified" toxins refers to these molecules when they are not associated with the other molecules with which they would be found in nature. Thus, reference to "isolated and purified" signifies the involvement of the "hand of man" as described herein. Chimeric toxins and genes also involve the "hand of man."

The use of oligonucleotide probes provides a method for identifying the toxins and genes of the subject invention, and additional novel genes and toxins. Probes provide a rapid method for identifying toxin-encoding genes. The nucleotide segments which are used as probes according to the invention can be synthesized using a DNA synthesizer and standard procedures, for example.

Chimeric toxins. Chimeric genes and toxins, produced by combining portions from subject invention.

Methods have been developed for making useful chimeric toxins by combining portions of B.t. crystal proteins. The portions which are combined need not, themselves, be pesticidal so long as the combination of portions creates a chimeric protein which is pesticidal. This can be done using restriction enzymes, as described in, for example, European Patent 0 228 838; Ge, A. Z., N. L. Shivarova, D. H. Dean (1989) *Proc. Natl. Acad. Sci. USA* 86:4037–4041; Ge, A. Z., D. Rivers, R. Milne, D. H. Dean (1991) *J. Biol. Chem.* 266:17954–17958; Schnepf, H. E., K. Tomczak. J. P. Ortega, H.R. Whiteley (1990) *J. Biol. Chem.* 265:20923–20930; Honee, G., D. Convents, J. Van Rie, S. Jansens, M. Peferoen, B. Visser (1991) *Mol. Microbiol.* 5:2799–2806. Alternatively, recombination using cellular recombination mechanisms can be used to achieve similar results. See, for example, Caramori, T., A. M. Albertini, A. Galizzi (1991) *Gene* 98:37–44; Widner, W. R., H. R. Whiteley (1990) *J. Bacteriol.* 172:2826–2832; Bosch, D., B. Schipper, H. van der Kliej, R. A. de Maagd, W. J. Stickema (1994) *Biotechnology* 12:915–918. A number of other methods are known in the art by which such chimeric DNAs can be made. The subject invention includes chimeric proteins that utilize the genes and toxins of the subject application.

Recombinant hosts. The toxin-encoding genes of the subject invention can be introduced into a wide variety of microbial or plant hosts. Expression of the toxin gene results, directly or indirectly, in the production and maintenance of the pesticide. With suitable microbial hosts, e.g., Pseudomonas, the microbes can be applied to the situs of the pest, where they will proliferate and be ingested. The result is a control of the pest. Alternatively, the microbe hosting the toxin gene can be killed and treated under conditions that prolong the activity of the toxin and stabilize the cell. The treated cell, which retains the toxic activity, then can be applied to the environment of the target pest.

Where the B.t. toxin gene is introduced via a suitable vector into a microbial host, and said host is applied to the environment in a living state, it is essential that certain host microbes be used. Microorganism hosts are selected which are known to occupy the "phytosphere" (phylloplane, phyllosphere, rhizosphere, and/or rhizoplane) of one or more crops of interest. These microorganisms are selected so as to be capable of successfully competing in the particular environment (crop and other insect habitats) with the wild-type microorganisms,provide for stable maintenance and expression of the gene expressing the polypeptide pesticide, and, desirably, provide for improved protection of the pesticide from environmental degradation and inactivation.

A large number of microorganisms are known to inhabit the phylloplane (the surface of the plant leaves) and/or the rhizosphere (the soil surrounding plant roots) of a wide variety of important crops. These microorganisms include bacteria, algae, and fungi. Of particular interest are microorganisms, such as bacteria, e.g., genera Pseudomonas, Erwinia, Serratia, Klebsiella, Xanthomonas, Streptomyces, Rhizobium, Rhodopseudomonas, Methylophilius, Agrobacterium, Acetobacter, Lactobacillus, Arthrobacter, Azotobacter, Leuconostoc, and Alcaligenes; fungi, particularly yeast, e.g., genera Saccharomyces, Cryptococcus, Kluyveromyces, Sporobolomyces, Rhodotorula, and Aureobasidium. Of particular interest are such phytosphere bacterial species as Pseudomonas syringae, *Pseudomonas fluorescens, Serratia marcescens, Acetobacter xylinum, Agrobacterium tumefaciens, Rhodopseudomonas spheroides, Xanthomonas campestris, Rhizobium melioti, Alcaligenes entrophus*, and *Azotobacter vinlandii*; and phytosphere yeast species such as Rhodotorula rubra, *R. glutinis, R. marina, R. aurantiaca, Cryptococcus albidus, C. diffluens, C. laurentii, Saccharomyces rosei, S. pretoriensis, S. cerevisiae, Sporobolomyces roseus, S. odorus, Kluyveromyces veronae*, and *Aureobasidium pollulans*. Of particular interest are the pigmented microorganisms.

A wide variety of methods are available for introducing a B.t. gene encoding a toxin into a microorganism host under conditions which allow for stable maintenance and expression of the gene. These methods are well known to those skilled in the art and are described, for example, in U.S. Pat. No. 5,135,867, which is incorporated herein by reference.

Control of homopterans using the isolates, toxins, and genes of the subject invention can be accomplished by a variety of methods known to those skilled in the art. These methods include, for example, the application of B.t. isolates to the pests (or their location), the application of recombinant microbes to the pests (or their locations), and the transformation of plants with genes which encode the pesticidal toxins of the subject invention. Recombinant microbes may be, for example, a B.t., *E. coli*, or Pseudomonas. Transformations can be made by those skilled in the art using standard techniques. Materials necessary for these transformations are disclosed herein or are otherwise readily available to the skilled artisan.

Synthetic genes which are functionally equivalent to the novel toxins of the subject invention can also be used to transform hosts. Methods for the production of synthetic genes can be found in, for example, U.S. Pat. No. 5,380,831.

Treatment of cells. As mentioned above, B.t. or recombinant cells expressing a B.t. toxin can be treated to prolong the toxin activity and stabilize the cell. The pesticide microcapsule that is formed comprises the B.t. toxin within a cellular structure that has been stabilized and will protect the toxin when the microcapsule is applied to the environment of the target pest. Suitable host cells may include either prokaryotes or eukaryotes, normally being limited to those cells which do not produce substances toxic to higher organisms, such as mammals. However, organisms which produce substances toxic to higher organisms could be used, where the toxic substances are unstable or the level of application sufficiently low as to avoid any possibility of toxicity to a mammalian host. As hosts, of particular interest will be the prokaryotes and the lower eukaryotes, such as fungi.

The cell will usually be intact and be substantially in the proliferative form when treated, rather than in a spore form, although in some instances spores may be employed.

Treatment of the microbial cell, e.g., a microbe containing the B.t. toxin gene, can be by chemical or physical means, or by a combination of chemical and/or physical means, so long as the technique does not deleteriously affect the properties of the toxin, nor diminish the cellular capability of protecting the toxin. Examples of chemical reagents are halogenating agents, particularly halogens of atomic no. 17–80. More particularly, iodine can be used under mild conditions and for sufficient time to achieve the desired results. Other suitable techniques include treatment with aldehydes, such as glutaraldehyde; anti-infectives, such as zephiran chloride and cetylpyridinium chloride; alcohols, such as isopropanol and ethanol; various histologic fixatives, such as Lugol iodine, Bouin's fixative, various acids and Helly's fixative (See: Humason, Gretchen L., *Animal Tissue Techniques*, W. H. Freeman and Company, 1967); or a combination of physical (heat) and chemical agents that preserve and prolong the activity of the toxin produced in the cell when the cell is administered to the host environment.

Examples of physical means are short wavelength radiation such as gamma-radiation and X-radiation, freezing, UV irradiation, lyophilization, and the like. Methods for treatment of microbial cells are disclosed in U.S. Pat. Nos. 4,695,455 and 4,695,462, which are incorporated herein by reference.

The cells generally will have enhanced structural stability which will enhance resistance to environmental conditions. Where the pesticide is in a proform, the method of cell treatment should be selected so as not to inhibit processing of the proform to the mature form of the pesticide by the target pest pathogen. For example, formaldehyde will crosslink proteins and could inhibit processing of the proform of a polypeptide pesticide. The method of treatment should retain at least a substantial portion of the bioavailability or bioactivity of the toxin.

Characteristics of particular interest in selecting a host cell for purposes of production include ease of introducing the B.t. gene into the host, availability of expression systems, efficiency of expression, stability of the pesticide in the host, and the presence of auxiliary genetic capabilities. Characteristics of interest for use as a pesticide microcapsule include protective qualities for the pesticide, such as thick cell walls, pigmentation, and intracellular packaging or formation of inclusion bodies; survival in aqueous environments; lack of mammalian toxicity; attractiveness to pests for ingestion; ease of killing and fixing without damage to the toxin; and the like. Other considerations include ease of formulation and handling, economics, storage stability and the like.

Growth of cells. The cellular host containing the B.t. insecticidal gene may be grown in any convenient nutrient medium, where the DNA construct provides a selective advantage, providing for a selective medium so that substantially all or all of the cells retain the B.t. gene. These cells may then be harvested in accordance with conventional ways. Alternatively, the cells can be treated prior to harvesting.

The B.t. cells of the invention can be cultured using standard art media and fermentation techniques. Upon completion of the fermentation cycle the bacteria can be harvested by first separating the B.t. spores and crystals from the fermentation broth by means well known in the art. Any B.t. spores and crystals can be recovered employing well-known techniques and used as a conventional δ-endotoxin B.t. preparation. For example, the spores and crystals can be formulated into a wettable powder, liquid concentrate, granules or other formulations by the addition of surfactants, dispersants, inert carriers, and other components to facilitate handling and application for particular target pests. These formulations and application procedures are all well known in the art. Alternately, the supernatant from the fermentation process can be used to obtain toxins according to the present invention. Soluble, secreted toxins are then isolated and purified employing well-known techniques.

Methods and formulations for control of pests. Control of homopterans using the isolates, toxins, and genes of the subject invention can be accomplished by a variety of methods known to those skilled in the art. These methods include, for example, the application of B.t. isolates to the pests (or their location), the application of recombinant microbes to the pests (or their locations), and the transformation of plants with genes which encode the pesticidal toxins of the subject invention. Recombinant microbes may be, for example, a B.t., *E. coli*, or Pseudomonas. Transformations can be made by those skilled in the art using standard techniques. Materials necessary for these transformations are disclosed herein or are otherwise readily available to the skilled artisan.

Formulated bait granules containing an attractant and toxins of the B.t. isolates, or recombinant microbes comprising the genes obtainable from the B.t. isolates disclosed herein, can be applied to the soil. Formulated product can also be applied as a seed-coating or root treatment or total plant treatment at later stages of the crop cycle. Plant and soil treatments of B.t. cells may be employed as wettable powders, granules or dusts, by mixing with various inert materials, such as inorganic minerals (phyllosilicates, carbonates, sulfates, phosphates, and the like) or botanical materials (powdered corncobs, rice hulls, walnut shells, and the like). The formulations may include spreader-sticker adjuvants, stabilizing agents, other pesticidal additives, or surfactants. Liquid formulations may be aqueous-based or non-aqueous and employed as foams, gels, suspensions, emulsifiable concentrates, or the like. The ingredients may include rheological agents, surfactants, emulsifiers, dispersants, or polymers.

As would be appreciated by a person skilled in the art, the pesticidal concentration will vary widely depending upon the nature of the particular formulation, particularly whether it is a concentrate or to be used directly. The pesticide will be present in at least 1% by weight and may be 100% by weight. The dry formulations will have from about 1–95% by weight of the pesticide while the liquid formulations will generally be from about 1–60% by weight of the solids in the liquid phase. The formulations will generally have from about $10^2$ to about $10^4$ cells/mg. These formulations that contain cells will be administered at about 50 mg (liquid or dry) to 1 kg or more per hectare.

The formulations can be applied to the environment of the pest, e.g., soil and foliage, by spraying, dusting, sprinkling, or the like.

Mutants. Mutants of novel isolates obtainable according to the invention can be made by procedures well known in the art. For example, an asporogenous mutant can be obtained through ethylmethane sulfonate (EMS) mutagenesis of an isolate. The mutants can be made using ultraviolet light and nitrosoguanidine by procedures well known in the art.

A smaller percentage of the asporogenous mutants will remain intact and not lyse for extended fermentation periods; these strains are designated lysis minus (−). Lysis minus strains can be identified by screening asporogenous mutants in shake flask media and selecting those mutants that are still intact and contain toxin crystals at the end of the fermentation. Lysis minus strains are suitable for a cell treatment process that will yield a protected encapsulated toxin protein.

To prepare a phage resistant variant of said asporogenous mutant, an aliquot of the phage lysate is spread onto nutrient agar and allowed to dry. An aliquot of the phage sensitive bacterial strain is then plated directly over the dried lysate and allowed to dry. The plates are incubated at 30° C. The plates are incubated for 2 days and, at that time numerous colonies could be seen growing on the agar. Some of these colonies are picked and subcultured onto nutrient agar plates. These apparent resistant cultures are tested for resistance by cross streaking with the phage lysate. A line of the phage lysate is streaked on the plate and allowed to dry. The presumptive resistant cultures are then streaked across the phage line. Resistant bacterial cultures show no lysis anywhere in the streak across the phage line after overnight incubation at 30 ° C. The resistance to phage is then reconfirmed by plating a lawn of the resistant culture onto a nutrient agar plate. The sensitive strain is also plated in the same manner to serve as the positive control. After drying, a drop of the phage lysate is placed in the center of the plate and allowed to dry. Resistant cultures showed no lysis in the area where the phage lysate has been placed after incubation at 30° C. for 24 hours.

Polynucleotide probes. It is well known that DNA possesses a fundamental property called base complementarity. In nature, DNA ordinarily exists in the form of pairs of anti-parallel strands, the bases on each strand projecting from that strand toward the opposite strand. The base adenine (A) on one strand will always be opposed to the base thymine (T) on the other strand, and the base guanine (G) will be opposed to the base cytosine (C). The bases are held in apposition by their ability to hydrogen bond in this specific way. Though each individual bond is relatively weak, the net effect of many adjacent hydrogen bonded bases, together with base stacking effects, is a stable joining of the two complementary strands. These bonds can be broken by treatments such as high pH or high temperature, and these conditions result in the dissociation, or "denaturation," of the two strands. If the DNA is then placed in conditions which make hydrogen bonding of the bases thermodynamically favorable, the DNA strands will anneal, or "hybridize," and reform the original double stranded DNA. If carried out under appropriate conditions, this hybridization can be highly specific. That is, only strands with a high degree of base complementarity will be able to form stable double stranded structures. The relationship of the specificity of hybridization to reaction conditions is well known. Thus, hybridization may be used to test whether two pieces of DNA are complementary in their base sequences. It is this hybridization mechanism which facilitates the use of probes to readily detect and characterize DNA sequences of interest.

The probes may be RNA or DNA. The probe will normally have at least about 10 bases, more usually at least about 18 bases, and may have up to about 50 bases or more, usually not having more than about 200 bases if the probe is made synthetically. However, longer probes can readily be utilized and such probes can be, for example, several kilobases in length. The probe sequence is designed to be at least substantially complementary to a portion of a gene encoding a toxin of interest. The probe need not have perfect complementarity to the sequence to which it hybridizes. The probes may be labelled utilizing techniques which are well known to those skilled in this art.

One useful hybridization procedure typically includes the initial steps of isolating the DNA sample of interest and purifying it chemically. Either lysed bacteria or total fractionated nucleic acid isolated from bacteria can be used. Cells can be treated using known techniques to liberate their DNA (and/or RNA). The DNA sample can be cut into pieces with an appropriate restriction enzyme. The pieces can be separated by size through electrophoresis in a gel, usually agarose or acrylamide. The pieces of interest can be transferred to an immobilizing membrane in a manner that retains the geometry of the pieces. The membrane can then be dried and prehybridized to equilibrate it for later immersion in a hybridization solution. The manner in which the nucleic acid is affixed to a solid support may vary. This fixing of the DNA for later processing has great value for the use of this technique in field studies, remote from laboratory facilities.

The particular hybridization technique is not essential to the subject invention. As improvements are made in hybridization techniques, they can be readily applied.

As is well known in the art, if the probe molecule and nucleic acid sample hybridize by forming a strong non-covalent bond between the two molecules, it can be reasonably assumed that the probe and sample are essentially identical. The probe's detectable label provides a means for determining in a known manner whether hybridization has occurred.

The polynucleotides of the subject invention, and probes derived from segments thereof, can be synthesized by use of DNA synthesizers using standard procedures. In the use of the nucleotide segments as probes, the particular probe is labeled with any suitable label known to those skilled in the art, including radioactive and non-radioactive labels. Typical radioactive labels include $^{32}P$, $^{35}S$, or the like. A probe labeled with a radioactive isotope can be constructed from a nucleotide sequence complementary to the DNA sample by a conventional nick translation reaction, using a DNase and DNA polymerase. The probe and sample can then be combined in a hybridization buffer solution and held at an appropriate temperature until annealing occurs. Thereafter, the membrane is washed free of extraneous materials, leaving the sample and bound probe molecules typically detected and quantified by autoradiography and/or liquid scintillation counting. For synthetic probes, it may be most desirable to use enzymes such as polynucleotide kinase or terminal transferase to end-label the DNA for use as probes.

Non-radioactive labels include, for example, ligands such as biotin or thyroxine, as well as enzymes such as hydrolases or perixodases, or the various chemiluminescers such as luciferin, or fluorescent compounds like fluorescein and its derivatives. The probes may be made inherently fluorescent as described in International Application No. WO93/16094. The probe may also be labeled at both ends with different types of labels for ease of separation, as, for example, by using an isotopic label at the end mentioned above and a biotin label at the other end.

The amount of labeled probe which is present in the hybridization solution will vary widely, depending upon the nature of the label, the amount of the labeled probe which can reasonably bind to the filter, and the stringency of the hybridization. Generally, substantial excesses of the probe will be employed to enhance the rate of binding of the probe to the fixed DNA.

Various degrees of stringency of hybridization can be employed. The more severe the conditions, the greater the complementarity that is required for duplex formation. Severity can be controlled by temperature, probe concentration, probe length, ionic strength, time, and the like. Preferably, hybridization is conducted under stringent conditions by techniques well known in the art, as described, for example, in Keller, G. H., M. M. Manak (1987) *DNA Probes*, Stockton Press, New York, N.Y., pp. 169–170.

As used herein "stringent" conditions for hybridization refers to conditions which achieve the same, or about the same, degree of specificity of hybridization as the conditions employed by the current applicants. Specifically, hybridization of immobilized DNA on Southern blots with 32P-labeled gene-specific probes was performed by standard methods (Maniatis et al.). In general, hybridization and subsequent washes were carried out under stringent conditions that allowed for detection of target sequences with homology to the subject toxin genes. For double-stranded DNA gene probes, hybridization was carried out overnight at 20–25° C. below the melting temperature (Tm) of the DNA hybrid in 6×SSPE, 5×Denhardt's solution, 0.1% SDS, 0.1 mg/ml denatured DNA. The melting temperature is described by the following formula (Beltz, G. A., K. A. Jacobs, T. H. Eickbush, P. T. Cherbas, and F. C. Kafatos [1983] *Methods of Enzymology*, R. Wu, L. Grossman and K. Moldave [eds.] Academic Press, New York 100:266–285).

$$Tm = 81.5°\,C. + 16.6 Log[Na+] + 0.41(\%G+C) - 0.61 (\%formamide) - 600/\text{length of duplex in base pairs}.$$

Washes are typically carried out as follows:

(1) Twice at room temperature for 15 minutes in 1×SSPE, 0.1% SDS (low stringency wash).

(2) Once at Tm−20° C. for 15 minutes in 0.2×SSPE, 0.1% SDS (moderate stringency wash).

For oligonucleotide probes, hybridization was carried out overnight at 10–20° C. below the melting temperature (Tm) of the hybrid in 6×SSPE, 5×Denhardt's solution, 0.1% SDS, 0.1 mg/ml denatured DNA. Tm for oligonucleotide probes was determined by the following formula:

$$Tm\,(°\,C.) = 2(\text{number T/A base pairs}) + 4(\text{number G/C base pairs})$$

(Suggs, S. V., T. Miyake, E. H. Kawashime, M. J. Johnson, K. Itakura, and R. B. Wallace [1981] *ICN-UCLA Symp. Dev. Biol. Using Purified Genes*, D. D. Brown [ed.], Academic Press, New York, 23:683–693).

Washes were typically carried out as follows:

(1) Twice at room temperature for 15 minutes 1×SSPE, 0.1% SDS (low stringency wash).

(2) Once at the hybridization temperature for 15 minutes in 1×SSPE, 0.1% SDS (moderate stringency wash).

Duplex formation and stability depend on substantial complementarity between the two strands of a hybrid, and, as noted above, a certain degree of mismatch can be tolerated. Therefore, the nucleotide sequences of the subject invention include mutations (both single and multiple), deletions, insertions, and combinations thereof, wherein said mutations, insertions and deletions permit formation of stable hybrids with the target polynucleotide of interest. Mutations, insertions, and deletions can be produced in a given polynucleotide sequence in many ways, and these methods are known to an ordinarily skilled artisan. Other methods may become known in the future.

The known methods include, but are not limited to:

(1) synthesizing chemically or otherwise an artificial sequence which is a mutation, insertion or deletion of the known sequence;

(2) using a nucleotide sequence of the present invention as a probe to obtain via hybridization a new sequence or a mutation, insertion or deletion of the probe sequence; and (3) mutating, inserting or deleting a test sequence in vitro or in vivo.

It is important to note that the mutational, insertional, and deletional variants generated from a given probe may be more or less efficient than the original probe. Notwithstanding such differences in efficiency, these variants are within the scope of the present invention.

Thus, mutational, insertional, and deletional variants of the disclosed nucleotide sequences can be readily prepared by methods which are well known to those skilled in the art. These variants can also be used as primer sequences so long as the variants have substantial sequence homology with the original sequence. As used herein, substantial sequence homology refers to homology which is sufficient to enable the variant to function in the same capacity as the original probe. Preferably, variants will have amino acid or nucleotide identity with the exemplified sequences that is greater than 50%; more preferably, there will be greater than 75% identity; and most preferably, there will be greater than 90% identity. The degree of homology needed for the variant to function in its intended capacity will depend upon the intended use of the sequence. It is well within the skill of a person trained in this art to make mutational, insertional, and deletional mutations which are designed to improve the function of the sequence or otherwise provide a methodological advantage.

PCR technology. Polymerase Chain Reaction (PCR) is a repetitive, enzymatic, primed synthesis of a nucleic acid sequence. This procedure is well known and commonly used by those skilled in this art (see Mullis, U.S. Pat. Nos. 4,683,195, 4,683,202, and 4,800,159; Saiki, Randall K., Stephen Scharf, Fred Faloona, Kary B. Mullis, Glenn T. Horn, Henry A. Erlich, Norman Arnheim [1985] "Enzymatic Amplification of β-Globin Genomic Sequences and Restriction Site Analysis for Diagnosis of Sickle Cell Anemia," *Science* 230:1350–354.). PCR is based on the enzymatic amplification of a DNA fragment of interest that is flanked by two oligonucleotide primers that hybridize to opposite strands of the target sequence. The primers are oriented with the 3' ends pointing towards each other. Repeated cycles of heat denaturation of the template, annealing of the primers to their complementary sequences, and extension of the annealed primers with a DNA polymerase result in the amplification of the segment defined by the 5' ends of the PCR primers. Since the extension product of each primer can serve as a template for the other primer, each cycle essentially doubles the amount of DNA fragment produced in the previous cycle. This results in the exponential accumulation of the specific target fragment, up to several million-fold in a few hours. By using a thermostable DNA polymerase such as Taq polymerase, which is isolated from the thermophilic bacterium *Thermus aquaticus*, the amplification process can be completely automated.

The DNA sequences obtainable according to the subject invention can be used as primers for PCR amplification. In performing PCR amplification a certain degree of mismatch can be tolerated between primer and template. Therefore, mutations, deletions, and insertions (especially additions of nucleotides to the 5' end) of primers obtained in light of the subject disclosure fall within the scope of the subject invention. Mutations, insertions and deletions can be produced in a given primer by methods known to an ordinarily skilled artisan. It is important to note that the mutational, insertional, and deletional variants generated from a given primer sequence may be more or less efficient than the original sequences. Notwithstanding such differences in efficiency, these variants are within the scope of the present invention.

All of the U.S. Patents referred to herein are hereby incorporated by reference.

Following are examples which illustrate procedures for practicing the invention. These examples should not be construed as limiting. All percentages are by weight and all solvent mixture proportions are by volume unless otherwise noted.

Example 1

Preparation of the Isolates

The B.t. strains were cultured in a peptone, glucose salts medium until they were fully sporulated. They were harvested by centrifugation and turned into a powder by lyophilization. Toxin proteins were extracted from the samples by extraction in a sodium carbonate, 2-mercaptoethanol buffer with a pH of 10.7 to 11.0 during extraction at 37° C. The protein extracts were recovered by centrifugation, dialyzed against 0.05 M sodium carbonate, pH 9.5, and if necessary, concentrated to at least 1 mg/ml protein using a "spin column" microconcentrator. Protein concentrations were estimated by laser densitometry using bovine serum albumin as a standard. Under these conditions, the extract from strain HD969 contained proteins ranging in size from 130 kDa to about 62 kDa (as well as a number of minor bands), PS66D3 had a major band at about 64 kDa and minor bands at about 52 kDa and 30 kDa, PS50C had a major band at about 62 kDa and numerous minor bands.

Example 2

Bioassay of Preparations Against *Nilaparvata lugens*, the Brown Rice Planthopper Bioassays consisted of exposing insects to artificial diet containing the B.t. preparations from Example 1 were diluted to 1 mg mL$^{-1}$ of the B.t. toxin. Insects, as nymphs, were exposed to the test solutions for 72 hours. After 24 hours any insects not feeding successfully, as judged by the failure to produce honeydew, were discarded. The insects were examined at 0, 24, 48 and 72 hours and the survival scored. Each bioassay was separately replicated three times with 10 insects being used in each replicate. Buffer controls, again using 10 insects, were run as part of each replicate bioassay. The results of these bioassays are presented in Table 3.

TABLE 3

| | | Percentage alive | | | |
|---|---|---|---|---|---|
| Sample | n | 0 h | 24 h | 48 h | 72 h |
| HD969 | 31 | 100 | 71 | 45 | 16 |
| 66D3 | 30 | 100 | 93 | 57 | 33 |
| 50C | 30 | 100 | 93 | 70 | 40 |
| buffer control a | 30 | 100 | 93 | 83 | 62 |
| buffer control b | 31 | 100 | 87 | 63 | 60 |
| buffer control c | 31 | 100 | 87 | 84 | 74 |

Example 3

Transformation of Plants

One aspect of the subject invention is the transformation of plants with genes encoding the insecticidal toxins of the subject invention. The transformed plants are resistant to attack by the target pests.

Genes encoding pesticidal toxins, as disclosed herein, can be inserted into plant cells using a variety of techniques which are well known in the art. For example, a large number of cloning vectors comprising a replication system in *E. coli* and a marker that permits selection of the transformed cells are available for preparation for the insertion of foreign genes into higher plants. The vectors comprise, for example, pBR322, pUC series. M13mp series, pACYC184, etc. Accordingly, the sequence encoding the B.t. toxin can be inserted into the vector at a suitable restriction site. The resulting plasmid is used for transformation into *E. coli*. The *E. coli* cells are cultivated in a suitable nutrient medium, then harvested and lysed. The plasmid is recovered. Sequence analysis, restriction analysis, electrophoresis, and other biochemical-molecular biological methods are generally carried out as methods of analysis. After each manipulation, the DNA sequence used can be cleaved and joined to the next DNA sequence. Each plasmid sequence can be cloned in the same or other plasmids. Depending on the method of inserting desired genes into the plant, other DNA sequences may be necessary. If, for example, the Ti or Ri plasmid is used for the transformation of the plant cell, then at least the right border, but often the right and the left border of the Ti or Ri plasmid T-DNA, has to be joined as the flanking region of the genes to be inserted.

The use of T-DNA for the transformation of plant cells has been intensively researched and sufficiently described in EP 120 516; Hoekema (1985) In: *The Binary Plant Vector System*, Offset-durkkerij Kanters B. V., Alblasserdam, Chapter 5; Fraley et al., *Crit. Rev. Plant Sci.* 4:1–46; and An et al. (1985) *EMBO J.* 4:277–287.

Once the inserted DNA has been integrated in the genome, it is relatively stable there and, as a rule, does not come out again. It normally contains a selection marker that confers on the transformed plant cells resistance to a biocide or an antibiotic, such as kanamycin, G 418, bleomycin, hygromycin, or chloramphenicol, inter alia. The individually employed marker should accordingly permit the selection of transformed cells rather than cells that do not contain the inserted DNA.

A large number of techniques are available for inserting DNA into a plant host cell. Those techniques include transformation with T-DNA using *Agrobacterium tumefaciens* or *Agrobacterium rhizogenes* as transformationagent, fusion, injection, biolistics (microparticle bombardment), or electroporation as well as other possible methods. If Agrobacteria are used for the transformation, the DNA to be inserted has to be cloned into special plasmids, namely either into an intermediate vector or into a binary vector. The intermediate vectors can be integrated into the Ti or Ri plasmid by homologous recombination owing to sequences that are homologous to sequences in the T-DNA. The Ti or Ri plasmid also comprises the vir region necessary for the transfer of the T-DNA. Intermediate vectors cannot replicate themselves in Agrobacteria. The intermediate vector can be transferred into *Agrobacterium tumefaciens* by means of a helper plasmid (conjugation). Binary vectors can replicate themselves both in *E. coli* and in Agrobacteria. They comprise a selection marker gene and a linker or polylinker which are framed by the right and left T-DNA border regions. They can be transformed directly into Agrobacteria (Holsters et al. [1978] *Mol. Gen. Genet.* 163 :181–187). The Agrobacterium used as host cell is to comprise a plasmid carrying a vir region. The vir region is necessary for the transfer of the T-DNA into the plant cell. Additional T-DNA may be contained. The bacterium so transformed is used for the transformation of plant cells. Plant explants can advantageously be cultivated with *Agrobacterium tumefaciens* or *Agrobacterium rhizogenes* for the transfer of the DNA into the plant cell. Whole plants can then be regenerated from the infected plant material (for example, pieces of leaf, segments of stalk, meristematic tissue, roots, but also protoplasts or suspension-cultivatedcells) in a suitable medium, which may contain antibiotics or biocides for selection. The plants so obtained can then be tested for the presence of the inserted DNA. No special demands are made of the plasmids in the case of injection and electroporation. It is possible to use ordinary plasmids, such as, for example, pUC derivatives. In biolistics transformation, plasmid DNA or linear DNA can be employed.

The transformed cells are regenerated into morphologically normal plants in the usual manner. If a transformation event involves a germ line cell, the inserted DNA and corresponding phenotypic trait(s) will be transmitted to progeny plants. Such plants can be grown in the normal manner and crossed with plants that have the same transformed hereditary factors or other hereditary factors. The resulting hybrid individuals have the corresponding phenotypic properties.

In a preferred embodiment of the subject invention, plants will be transformed with genes wherein the codon usage has been optimized for plants. See, for example, U.S. Pat. No. 5,380,831. Also, advantageously, plants encoding a truncated toxin will be used. The truncated toxin typically will encode about 55% to about 80% of the full length toxin. Methods for creating synthetic B.t. genes for use in plants are known in the art.

It should be understood that the examples and embodiments described herein are for illustrative purposes only and that various modifications or changes in light thereof will be suggested to persons skilled in the art and are to be included within the spirit and purview of this application and the scope of the appended claims.

We claim:

1. A method for controlling a homopteran insect pest, wherein said method comprises contacting said pest with a toxin, other than a Cry1Ac toxin and other than a Cry1C toxin, obtainable from *Bacillus thuringiensis* isolate HD969.

2. The method, according to claim 1, wherein said toxin is expressed in a plant.

3. A method for controlling a homopteran insect pest, wherein said method comprises contacting said pest with a Cry1B toxin obtainable from *Bacillus thuringiensis* isolate HD969.

* * * * *

UNITED STATES PATENT AND TRADEMARK OFFICE
CERTIFICATE OF CORRECTION

PATENT NO. : 6,051,550
DATED : April 18, 2000
INVENTOR(S) : H. Ernest Schnepf and Brian Stockhoff It is certified that error appears in the above-identified patent and that said Letters Patent is hereby corrected as shown below:

Column 4, line 46: "HID969" should read --HD969--.

Column 6, lines 66-67: "from subject invention." should read --from more than one Bt toxin or gene, may also be utilized according to the teachings of the subject invention.--.

Column 7, line 10: "Tomczak. J.P." should read --Tomczak, J.P.--.

Column 10, line 61: "Iysate" should read --lysate--.

Column 14, line 14: "230:1350-354.)." should read --230:1350-1354.).--.

Signed and Sealed this

Twenty-fourth Day of April, 2001

*Attest:*

NICHOLAS P. GODICI

*Attesting Officer*     *Acting Director of the United States Patent and Trademark Office*